United States Patent
Mangiardi

(10) Patent No.: US 10,022,164 B2
(45) Date of Patent: Jul. 17, 2018

(54) ORTHOPEDIC FASTENER DEVICE

(71) Applicant: EVENTIONS, LLC, Charlotte, NC (US)

(72) Inventor: Eric K. Mangiardi, Charlotte, NC (US)

(73) Assignee: EVENTIONS, LLC, Charlotte, NC (US)

(*) Notice: Subject to any disclaimer, the term of this patent is extended or adjusted under 35 U.S.C. 154(b) by 41 days.

(21) Appl. No.: 14/203,099

(22) Filed: Mar. 10, 2014

(65) Prior Publication Data

US 2014/0194877 A1 Jul. 10, 2014

Related U.S. Application Data

(63) Continuation-in-part of application No. 12/539,314, filed on Aug. 11, 2009, now abandoned, which is a
(Continued)

(51) Int. Cl.
| | |
|---|---|
| *A61B 17/56* | (2006.01) |
| *A61F 2/06* | (2013.01) |
| *A61B 17/72* | (2006.01) |
| *A61B 17/86* | (2006.01) |
| *A61B 17/84* | (2006.01) |
| *A61L 31/02* | (2006.01) |

(Continued)

(52) U.S. Cl.
CPC .......... *A61B 17/72* (2013.01); *A61B 17/7233* (2013.01); *A61B 17/7258* (2013.01); *A61B 17/848* (2013.01); *A61B 17/866* (2013.01); *A61L 31/022* (2013.01); *A61L 31/10* (2013.01); *A61L 31/148* (2013.01); *A61B 17/7291* (2013.01); *A61B 2017/00004* (2013.01); *A61B 2017/00898* (2013.01); *A61B 2017/681* (2013.01)

(58) Field of Classification Search
CPC ............. A61L 2300/606; A61L 31/145; A61L 17/145; A61L 2300/00; A61B 17/72; A61B 17/7233; A61B 2017/00004; A61B 17/7208; A61B 17/68; A61B 17/84
See application file for complete search history.

(56) References Cited

U.S. PATENT DOCUMENTS

| | | |
|---|---|---|
| 4,642,104 A | 2/1987 | Sakamoto et al. |
| 5,520,664 A | 5/1996 | Bricault et al. |
| | (Continued) | |

OTHER PUBLICATIONS

Yuan et al., "Characterization of Poly(L-lactic acid) Fibers Produced by Melt Spinning," Journal of Applied Polymer Science, 2001, pp. 251-260, vol. 81.

(Continued)

*Primary Examiner* — Ann Schillinger
(74) *Attorney, Agent, or Firm* — Ping Wang; Morris, Manning & Martin, LLP

(57) ABSTRACT

Orthopedic fastener devices for fixation of fractured bones are disclosed. The orthopedic fastener device is in the form of an orthopedic fastener having an IM nail coated on its external surface with a bioabsorbable or biodegradable hydrogel. Also disclosed are hydrogel coated orthopedic fastener devices in the form of a K-wire or bone screw, a method for stabilizing a fractured long bone fracture by inserting an orthopedic fastener into the medullary canal of the bone and a kit for fastener implantation.

11 Claims, 7 Drawing Sheets

Related U.S. Application Data continuation-in-part of application No. 12/417,122, filed on Apr. 2, 2009, now Pat. No. 8,246,691.

(60) Provisional application No. 61/129,203, filed on Jun. 11, 2008.

(51) Int. Cl.
*A61L 31/10* (2006.01)
*A61L 31/14* (2006.01)
*A61B 17/00* (2006.01)
*A61B 17/68* (2006.01)

(56) References Cited

U.S. PATENT DOCUMENTS

| | | | |
|---|---|---|---|
| 5,522,881 A | 6/1996 | Lentz | |
| 5,529,736 A * | 6/1996 | Shalaby et al. | 264/162 |
| 5,645,592 A * | 7/1997 | Nicolais et al. | 606/63 |
| 5,653,745 A | 8/1997 | Trescony | |
| 5,827,321 A | 10/1998 | Roubin et al. | |
| 5,843,172 A | 12/1998 | Yan | |
| 6,124,273 A * | 9/2000 | Drohan | A61K 9/0014 514/13.6 |
| 6,214,037 B1 | 4/2001 | Mitchell et al. | |
| 6,296,645 B1 * | 10/2001 | Hover et al. | 606/62 |
| 6,752,829 B2 | 6/2004 | Kocur et al. | |
| 7,131,992 B2 | 11/2006 | Iwasaka et al. | |
| 7,338,530 B2 | 3/2008 | Carter et al. | |
| 7,875,069 B2 | 1/2011 | Heaney et al. | |
| 7,988,716 B2 | 8/2011 | Schwartz | |
| 8,016,880 B2 | 9/2011 | Cook et al. | |
| 8,414,907 B2 | 4/2013 | Molz et al. | |
| 2001/0031274 A1 * | 10/2001 | Schmidmaier et al. | 424/428 |
| 2002/0151898 A1 * | 10/2002 | Sohngen et al. | 606/62 |
| 2003/0040754 A1 | 2/2003 | Mitchell et al. | |
| 2005/0038501 A1 | 2/2005 | Moore et al. | |
| 2005/0080478 A1 | 4/2005 | Barongan | |
| 2005/0085891 A1 | 4/2005 | Goto et al. | |
| 2005/0090888 A1 | 4/2005 | Hines et al. | |
| 2005/0119730 A1 | 6/2005 | Howat et al. | |
| 2005/0125072 A1 | 6/2005 | Kolb | |
| 2005/0187555 A1 | 8/2005 | Biedermann et al. | |
| 2005/0220837 A1 * | 10/2005 | Disegi et al. | 424/423 |
| 2006/0100689 A1 | 5/2006 | Pryor | |
| 2006/0265054 A1 | 11/2006 | Greenhalgh et al. | |
| 2007/0129787 A1 | 6/2007 | Bezwada | |
| 2007/0270939 A1 | 11/2007 | Hood et al. | |
| 2007/0293963 A1 | 12/2007 | Jung et al. | |
| 2008/0015578 A1 * | 1/2008 | Erickson et al. | 606/61 |
| 2008/0140176 A1 | 6/2008 | Krause et al. | |
| 2008/0200976 A1 | 8/2008 | Asgari | |
| 2008/0254125 A1 * | 10/2008 | Freier | 424/488 |
| 2008/0288047 A1 | 11/2008 | Friebe et al. | |
| 2008/0319536 A1 | 12/2008 | Houston et al. | |
| 2009/0024204 A1 | 1/2009 | Greenhalgh et al. | |
| 2009/0076591 A1 | 3/2009 | Girton et al. | |
| 2009/0187240 A1 | 7/2009 | Clerc et al. | |
| 2009/0204082 A1 | 8/2009 | Wesselmann et al. | |
| 2010/0004733 A1 | 1/2010 | Atanasoska et al. | |
| 2010/0174367 A1 | 7/2010 | Janko et al. | |
| 2010/0256729 A1 | 10/2010 | Mangiardi | |
| 2010/0256731 A1 | 10/2010 | Mangiardi | |

OTHER PUBLICATIONS

Carlson et al., "Anti-biofilm properties of chitosan-coated surfaces" Journal of Biomaterials Science Polymer Education, 2008, pp. 1035-1046, vol. 19—No. 8.

Van De Velde et al., "Bipolymers: overview of several properties and consequences on their applications," Polymer Testing, 2002, pp. 433-442, vol. 21.

Donelli et al., "Plastic Biliary Stent Occlusion: Factors Involved and Possible Preventive Approaches," Journal of Clinical Medicine & Research, Mar. 2007, pp. 53-60, vol. 5—No. 1.

Somogyi et al., "Biliary and pancreatic stents," Gastrointestinal Endoscopy, 2006, pp. 910-919, vol. 63—No. 7.

International Search Report and Written Opinion of the International Searching Authority issued in International Patent Application Serial No. PCT/US2009/069786 dated Aug. 25, 2010.

File history of U.S. Appl. No. 12/539,314, filed Aug. 11, 2009.

File history of U.S. Appl. No. 12/417,122, filed Apr. 2, 2009.

International Search Report and Written Opinion of the International Searching Authority of International Application No. PCT/US2014/022676 dated Nov. 20, 2014.

European Search Report issued in European Patent Application No. 09842845.1 dated Feb. 18, 2015.

\* cited by examiner

ORTHOPEDIC FASTENER DEVICE

This application is a continuation-in-part application of U.S. patent application Ser. No. 12/539,314, filed Aug. 11, 2009, which is a continuation-in-part application of U.S. patent application Ser. No. 12/417,122, filed Apr. 2, 2009, now U.S. Pat. No. 8,246,691, which claims priority to U.S. Patent Application Ser. No. 61/129,203, filed Jun. 11, 2008. The entirety of all of the aforementioned applications is incorporated herein by reference.

FIELD

The present invention generally relates to medical devices and, in particular, to orthopedic fastener devices for the fixation of bone fragments.

BACKGROUND

There are about 500,000 fractures of the tibia and fibula, 200,000 metacarpal fractures and over 400,000 distal radial fractures in the United States each year. In many cases the bones are immobilized by placing a cast on the fractured limb. However, casts often must immobilize a substantial length of the limb, can be heavy, inconvenient and limit the use of the limb, including significantly limiting the mobility of the subject. Additionally, there is a risk of non-union of the fractured ends, resulting in a failure of the fractured ends to unite. Non-unions may require additional operations to promote fracture healing. In addition to the risk of general anesthesia and early post-operative venous thromboembolism complications in patients who require re-operation face additional rehabilitation and time off from work.

Another means for fixation of long bone fragments includes the use of Kirschner wires (K-wires) drilled into the bone fragments and held in place by an external fixation device. However, external fixation devices may not be practical in all situations, as they may interfere with some functions. Additionally, because K-Wires pass through the skin, extended presence of conventional K-Wires may form a potential passage for bacteria and cause infection. Additionally, conventional K-Wires can migrate, causing a loss of fixation of the bone fragments.

Still another means for fixation of long bone fragments includes the insertion of an intramedullary (IM) nail into the lumen, or medullary cavity, of the long bone. The IM nail spans the fracture and is secured to the bone on either side by screws through the bone. IM nails are typically manufactured from a durable metal material and may be left in the bone after healing. In some instances, however, surgical removal of a durable IM nail is required, again exposing a subject to the risks of general anesthesia, venous thromboembolism, rehabilitation and time off from work. Additionally, present IM nails do not fill up the entire width of the lumen in the bone, potentially allowing the fracture to unite in a displaced, off-set or crooked manner, resulting in improper healing of the fracture. Accordingly, there exists a need for an improved IM nail in the form of an orthopedic fastener that is biodegradable and fills the lumen to prevent off-set healing of the fracture.

SUMMARY

One aspect of the present application relates to an orthopedic fastener for internal fixation of a fractured long bone, comprising an IM nail coated on its external surface with a bioabsorbable or biodegradable hydrogel.

Another aspect of the present application relates to a method for stabilizing a bone fracture. The method includes inserting an orthopedic fastener comprising an IM nail coated on its external surface with a bioabsorbable or biodegradable hydrogel into the canal of a bone having a fracture.

Still another aspect of the present application relates to a kit for orthopedic fastener implantation in a fractured long bone. The kit includes: an orthopedic fastener comprising an IM nail coated on its external surface with a bioabsorbable or biodegradable hydrogel; a guide wire or rod; and a pusher tube that is movable along or over the guide wire or rod.

Still another aspect of the present application relates to an orthopedic fastener device for fixation of a fractured bone comprising a K-Wire coated on its external surface with a bioabsorbable or biodegradable hydrogel.

Still another aspect of the present application relates to an orthopedic fastener device for fixation of a fractured bone comprising a bone screw coated on its external surface with a bioabsorbable or biodegradable hydrogel.

BRIEF DESCRIPTION OF DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 5A is a side plane view. FIG. 5B is a side cross sectional view.

FIG. 6A is a side plane cross sectional view. FIG. 6B is a cross sectional view from an end of the bone.

FIG. 7A is a side plane cross sectional view. FIG. 7B is a cross sectional view from an end of the bone.

DETAILED DESCRIPTION

Figure 1:
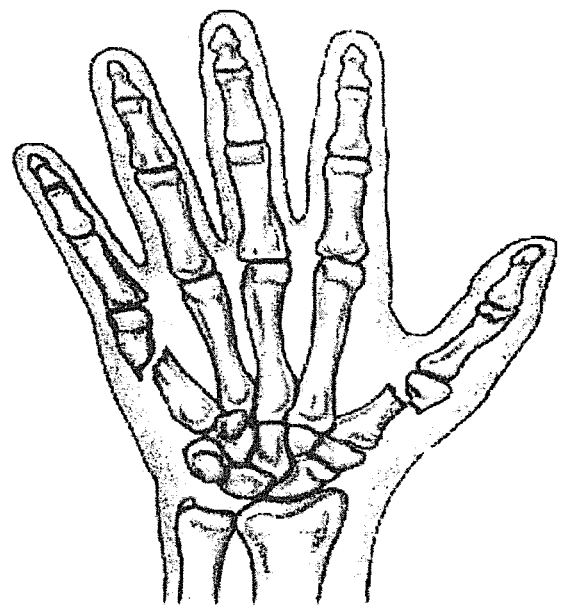
FIG. 1 shows an exemplary illustration of a displaced metacarpal fracture.

The practice of the present invention will employ, unless otherwise indicated, conventional medical devices and methods within the skill of the art. Such techniques are explained fully in the literature. All publications, patents and patent applications cited herein, whether supra or infra, are hereby incorporated by reference in their entirety.

The present application relates to an orthopedic fastener device for the fixation of bone fragments or bone fractures. The orthopedic fastener device contains an elongated metal or alloy body coated with a hydrogel. In certain embodiments, the orthopedic fastener device is an orthopedic fastener coated with a hydrogel. In other embodiments, the orthopedic fastener device is a K-wire coated with a hydrogel. In yet other embodiments, the orthopedic fastener device is a bone screw coated with a hydrogel.

As used herein, the term "fastener" refers to something that attaches or joins two parts together. In some embodiments, a fastener is a hardware device that mechanically joins or affixes two or more objects together. As used herein, the term "orthopedic fastener" refers to a fastener device which is implanted within the hollow center of a fractured bone to stabilize and/or reinforce the fractured bone.

As used herein, the term "long bone" refers to any bone having a shaft and two extremities. Long bones are found in the limbs and include the clavicle, humerus, radius, ulna, femur, tibia, fibula, metacarpal and metatarsal bones.

One aspect of the present application relates to an orthopedic fastener for internal fixation of a fractured long bone comprising an IM nail coated on its external surface with a bioabsorbable or biodegradable hydrogel.

In some embodiments, the IM nail comprises a center lumen to accommodate a guide wire.

In particular embodiments, the orthopedic fastener degrades in situ by hydrolytic reactions, enzymatic reactions, alkaline or pH changes.

In some embodiments, the IM nail is manufactured from a biodegradable metal or biodegradable alloy. In further embodiments, the biodegradable metal is magnesium. In other further embodiments, the biodegradable alloy comprises magnesium. In still other, or related, further embodiments, the biodegradable alloy comprises rare earth materials. In yet still other, or related, further embodiments, the biodegradable alloy comprises a magnesium alloy and chitin. In yet still other embodiments, the biodegradable alloy comprises a magnesium and chitin alloy.

In some embodiments, the IM nail is made of a chitin and chitosan, N-acylchitosan hydrogel and magnesium alloy with rare earth elements.

In particular embodiments, the hydrogel is a chitin chitosan, N-acylchitosan hydrogel.

In some embodiments, the hydrogel swells to about 30% of its maximal diameter within 10 minutes after coming in contact with moisture.

Another aspect of the present application relates to a method for stabilizing a bone fracture comprising, inserting an orthopedic fastener into the medullary canal of a bone having a fracture, wherein said orthopedic fastener comprises an IM nail coated on its external surface with a bioabsorbable or biodegradable hydrogel.

In some embodiments, the orthopedic fastener is placed through the bone cortex.

In particular embodiments, the orthopedic fastener degrades in situ by hydrolytic reactions, enzymatic reactions, alkaline or pH changes.

Yet another aspect of the present application relates to a kit for fastener implantation in a fractured long bone, said kit comprising: an orthopedic fastener comprising an IM nail coated on its external surface with a bioabsorbable or biodegradable hydrogel; a guide wire or rod; and a pusher that is movable along or over the guide wire or rod.

In some embodiments, the IM nail is made of a bioabsorbable material.

In particular embodiments, the IM nail further comprises a center lumen to accommodate the guide wire.

In some embodiments, the IM nail is made of a magnesium alloy and chitin.

In some embodiments, the IM nail is made of a magnesium and chitin alloy.

In other embodiments, the IM nail is made with a magnesium core coated with a chitin chitosan, N-acylchitosan hydrogel outer layer.

In still other embodiments, the IM nail is made of a chitin and chitosan, N-acylchitosan hydrogel and magnesium alloy with raw earth elements.

Still another aspect of the present application relates to an orthopedic fastener device for fixation of a fractured bone comprising a K-Wire coated on its external surface with a bioabsorbable or biodegradable hydrogel.

Yet still another aspect of the present application relates to an orthopedic fastener device for fixation of a fractured bone, comprising a bone screw coated on its external surface with a bioabsorbable or biodegradable hydrogel.

In some embodiments, the bone screw is a Scaphoid screw for fixation of a fractured carpal or tarsal bone.

For reference, FIG. 1 shows an illustration of a hand having displaced fractures of the first and fifth metacarpal bones.

Figure 2:
FIG. 2 shows an X-Ray image of an example of a displaced ulnar fracture.

FIG. 2 is an exemplary X-ray image of a forearm having a displaced fracture of the radius.

Figure 3:
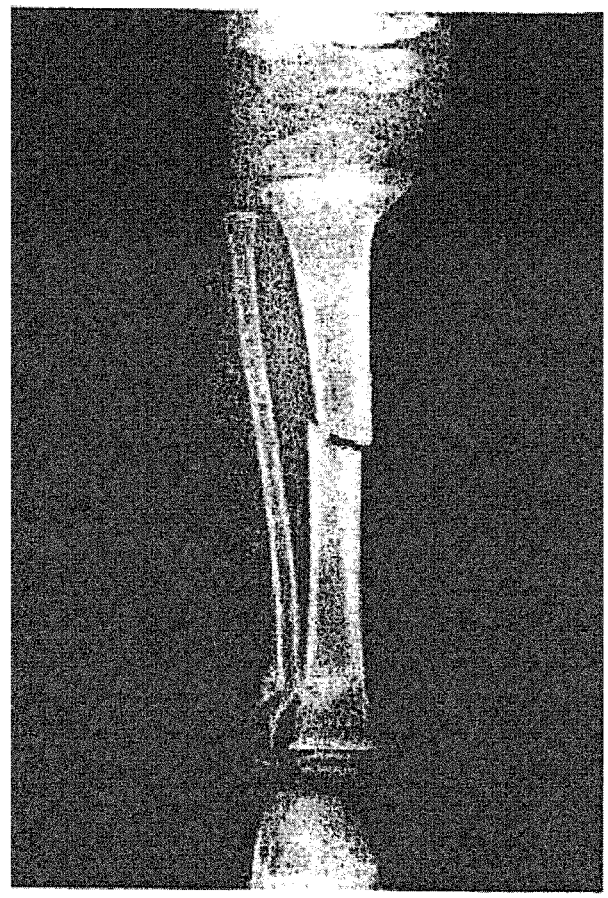
FIG. 3 shows an X-Ray image of an example of a displaced tibia fracture.

FIG. 3 is an exemplary X-ray image of a lower leg having a displaced fracture of the tibia.

IM Nail

One aspect of the present application relates to an orthopedic fastener for internal fixation of a fractured long bone, comprising an IM nail coated on its external surface with a bioabsorbable or biodegradable hydrogel. The hydrogel swells after implant of the orthopedic fastener, creating an internal soft fixation of the fracture, assisting with the realignment of displaced fractures. The hydrogel degrades over time based upon enzymatic or pH interaction with the subject's internal milieu. Accordingly, no subsequent or repeat surgical procedures are required to remove the hydrogel.

As used herein, the term "intramedullary nail (IM nail)," also known as "intramedullary rod," "inter-locking nail" or "Kiintscher nail," is a metal rod or tube forced into the medullary cavity of a bone. IM nails have long been used to treat fractures of long bones of the body. The IM nail can be manufactured from durable metal materials or from biodegradable metals or metal alloys as used in other biodegradable fasteners described herein.

Figure 4:
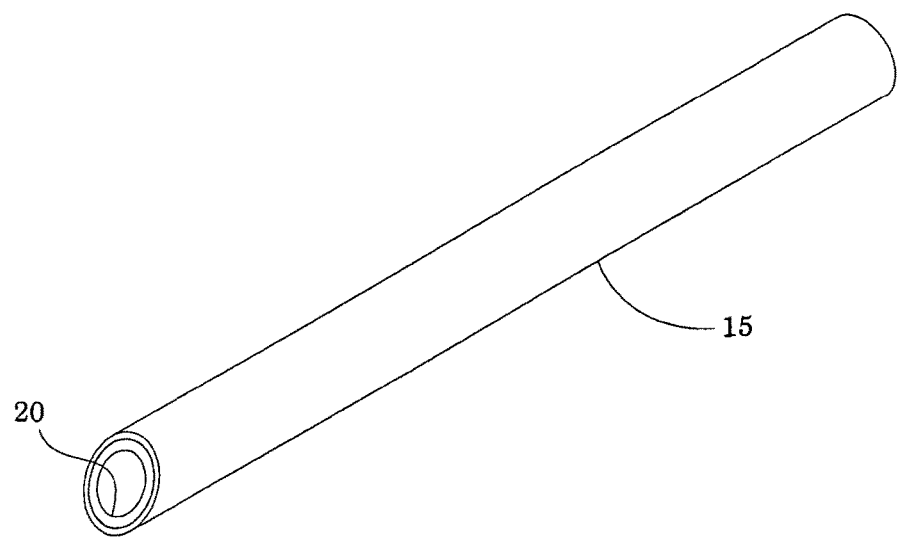
FIG. 4 is an isometric view of an exemplary orthopedic fastener.

FIG. 4 is an isometric view of an exemplary orthopedic fastener 10 for internal fixation of a fractured long bone. The orthopedic fastener comprises an IM nail 20 coated on its external surface with a bioabsorbable or biodegradable hydrogel 15.

Figure 5A:
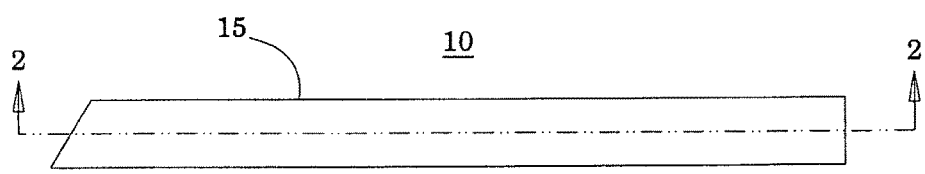
FIGS. 5A and 5B show an exemplary orthopedic fastener.
Figure 5B:
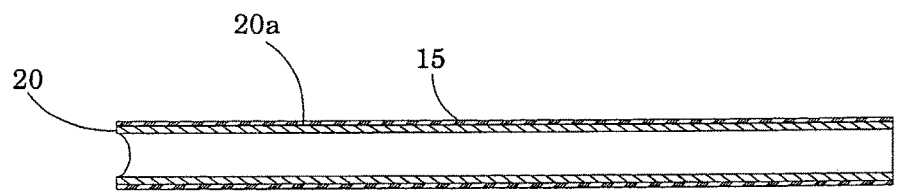

FIG. 5A is a side plane view of the exemplary orthopedic fastener of FIG. 4, while FIG. 5B is a side cross sectional view of the exemplary orthopedic fastener as viewed in the direction of the arrows when bisected at line 2-2. The orthopedic fastener comprises an IM nail 20 coated on its external surface 20a with a bioabsorbable or biodegradable hydrogel 15

Figure 6A:
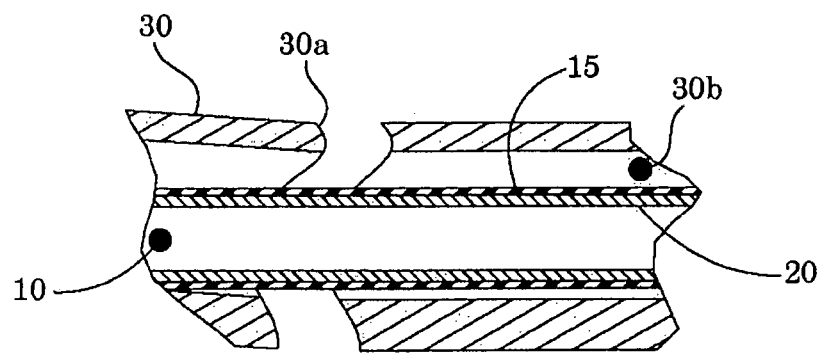
FIGS. 6A and 6B show an exemplary orthopedic fastener as applied to a displaced long bone fracture.
Figure 6B:
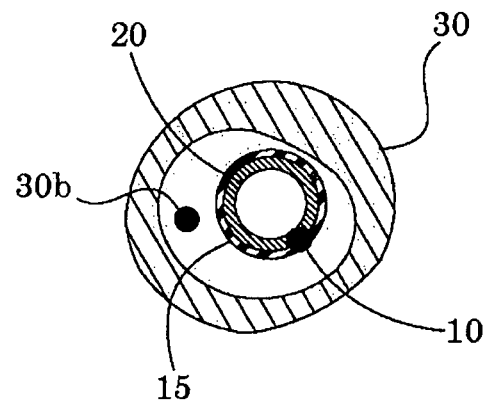

The hydrogel 15 swells after implant of the orthopedic fastener 10, creating an internal soft fixation of the fracture, assisting with the realignment of displaced fracture as illustrated in FIGS. 6A and 6B.

In FIG. 6A the displaced fracture 30a of the long bone 30 is illustrated in a side plane cross sectional view, with orthopedic fastener 10 positioned in the medullary cavity 30b. FIG. 6B further illustrates, in a cross-sectional view from an end of the bone, the orthopedic fastener 10 placement in the medullary cavity 30b prior to expansion of the hydrogel 15.

Figure 7A:
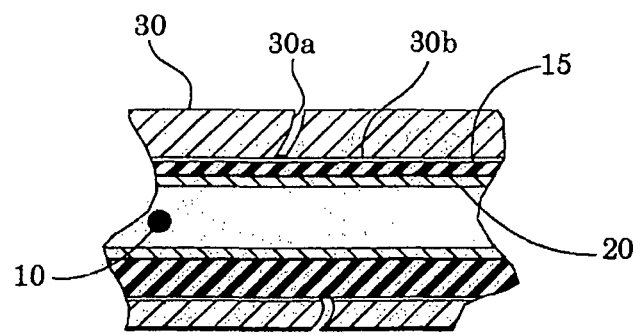
FIGS. 7A and 7B show an exemplary orthopedic fastener in final state as applied to a displaced long bone fracture.
Figure 7B:
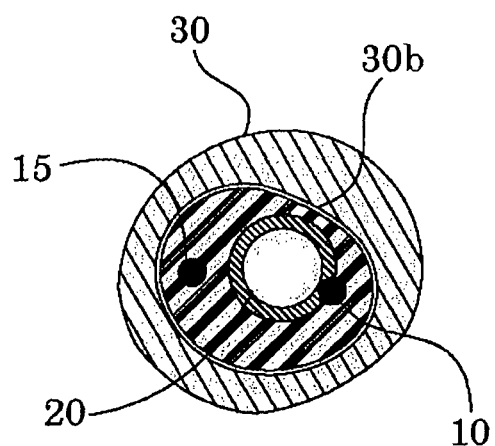

In FIG. 7A, the orthopedic fastener 10 is illustrated in a side plane cross sectional view with the expansion of the hydrogel 15, comprising the realignment of the displaced fracture 30a of the fractured long bone 30. The cross-sectional view from an end of the bone in FIG. 7B further illustrates the orthopedic fastener 10 with expanded hydrogel 15 in the medullary cavity 30b. The hydrogel 15 degrades over time based upon enzymatic or pH interaction with the subject's internal milieu. Accordingly, no subsequent or repeat surgical procedures are required to remove the hydrogel.

The fastener body may further include a center lumen to accommodate a guide wire. This center lumen may provide additionally flow throughput after the removal of guide wire.

In a particular embodiment, the orthopedic fastener is imbedded with barium sulphate or other metallic particles or contrast agents to enhance imaging.

In some embodiments, the orthopedic fastener is coated with a biodegradable material to control its properties, including mechanical strength, biocompatibility, biodegradation, diffusibility, and absorption properties.

In particular embodiments, the IM nail is tubular. In a related embodiment, the IM nail further contains a center lumen. In other particular embodiments, the IM nail is V-shaped.

In some embodiments, the orthopedic fastener degrades in situ by hydrolytic reactions, enzymatic reactions, alkaline or pH changes.

In some embodiments, the IM nail is manufactured from a durable metal. In a further embodiment, the durable metal is titanium. In another further embodiment, the durable metal is an alloy comprising titanium. In a still further embodiment, the alloy comprises titanium and nickel. In a yet still further embodiment, the alloy comprising titanium and nickel is nitinol.

In some embodiments, the IM nail is manufactured from a biodegradable metal or biodegradable alloy. In a further embodiment, the biodegradable metal is magnesium. In another further embodiment, the biodegradable alloy comprises magnesium. In a still further embodiment, the magnesium alloy additionally includes rare earth materials. In another or related still further embodiment, the biodegradable alloy comprises a magnesium and chitin alloy. In another or related still further embodiment, the biodegradable alloy comprises a magnesium alloy and chitin. In a yet further embodiment, the IM nail is made of a chitin and chitosan, N-acylchitosan hydrogel and magnesium alloy with rare earth elements.

In some embodiments, the hydrogel is a chitin chitosan, N-acylchitosan hydrogel. In particular embodiments, the hydrogel may absorb moisture and expand in situ at the treatment site. For example, the hydrogel would swell once it comes into contact with various body fluids. As used herein, the "pre-implantation diameter Dpre" refers to the largest diameter of an orthopedic fastener body before implantation and the "post-implantation diameter Dpost" refers to the largest diameter of the orthopedic fastener body after implantation.

In some embodiments, the hydrogel swells to about 10-90%, 10-70% or 10-50% of its maximal diameter within 10, 20 or 30 minutes after coming in contact with moisture. In some embodiments, the hydrogel swells to about 10% of its maximal diameter within 10, 20 or 30 minutes after coming in contact with moisture. In some embodiments, the hydrogel swells to about 20% of its maximal diameter within 10, 20 or 30 minutes after coming in contact with moisture. In some embodiments, the hydrogel swells to about 30% of its maximal diameter within 10, 20 or 30 minutes after coming in contact with moisture. In some embodiments, the hydrogel swells to about 40% of its maximal diameter within 10, 20 or 30 minutes after coming in contact with moisture. In some embodiments, the hydrogel swells to about 50% of its maximal diameter within 10, 20 or 30 minutes after coming in contact with moisture. The hydrogel swells or expands by absorbing of fluids and improves the connection and support of the inner wall of the bone canal.

In another embodiment, the orthopedic fastener is imbedded or coated with barium sulphate or other contrast agents to enhance imaging of the fastener.

In another embodiment, the orthopedic fastener is additionally coated with a biodegradable material to control its properties, including mechanical strength, biocompatibility, biodegradation, diffusibility, and absorption properties.

In another embodiment, the orthopedic fastener degrades in situ by hydrolytic reactions, enzymatic reactions, alkaline or pH changes.

The shape, length and diameter of the orthopedic fastener are application dependent. The elongated fastener body can be straight or curved or in the shape to match the curvature of a particular bone. Each type of orthopedic fastener is designed to fit within a specific bone. Therefore, the shape, length, and diameter of fasteners differ by type to accommodate and support different sized lumens and different clinical needs. For example, each major orthopedic fastener application, such as clavicle, humerus, radius, ulna, femur, tibia, fibula, metacarpal or metatarsal, requires a different diameter and shape to enable placement, to remain in place after placement, to stabilize and support the bone it is placed in, and to allow conformance to the normal anatomy.

As used herein, the diameter of a fastener refers to the width across the shaft of the fastener body, which is also referred to as the "major diameter." In one embodiment, the fastener has a uniform diameter. In another embodiment, the fastener has a variable diameter. In one embodiment, the diameter at the distal end is smaller than the diameter at the proximal end. In another embodiment, the diameter at the proximal end is smaller than the diameter at the distal end. In yet another embodiment, the diameters at the distal end and the proximal end are both smaller than the diameter at the middle section of the fastener. In cases where a fastener has a variable diameter, the "major diameter" is the largest diameter along the fastener body.

As used herein, the term "maximal diameter" of a hydrogel coated fastener refers to the maximum width across the shaft of the fastener body after the hydrogel coating of the fastener is fully hydrated.

In one embodiment, the fastener is delivered to the treatment site in a medullary canal with a pusher rod that pushes the fastener through a hole drilled in one end of the bone. The pusher rod travels over a guide wire. The pusher rod is designed in such a way to attach to the ends of the fastener to assist with directing the delivery. In one embodiment, the pusher rod interlocks with the proximal end of the fastener in a male/female fashion, much the same way a wrench fits over a nut.

In some embodiments, the IM nail may also be made with a bioabsorbable non-metal material. Examples of bioabsorbable non-metal materials include, but are not limited to, polylactic acid or polylactide (PLA), polyglycolic acid or polyglycolide (PGA), poly-ε-caprolactone (PCL), polyhydroxybutyrate (PHB), and co-polymers thereof.

In one embodiment, the bioabsorbable material of the fastener and/or hydrogel is degraded based on varying levels of pH. For example, the material may be stable at a neutral pH but degrades at a high pH. Examples of such materials include, but are not limited to chitin and chitosan. In another embodiment, the bioabsorbable material is degradable by enzymes, such as lysozymes.

In another embodiment, the bioabsorbable material is embedded with, or configured to carry, various agents or cells. The agents may be coupled to the outer and/or inner surfaces of the orthopedic fastener body or integrated into the bioabsorbable material of the hydrogel. In one embodiment, the fastener has a hollow center lumen so that agents may be placed inside the lumen to increase the dose release. The fastener can additionally have multiple reservoirs, one inside the other, so that when the outer layer is absorbed the next reservoir is exposed and a further release of a larger dose of the chosen agents or cells. The chosen agent or cells may also be mixed with the polymer for sustained release.

Examples of agents that can be embedded into or carried by a fastener include, but are not limited to, small molecule drugs, biologicals and gene transfer vectors.

Examples of biologicals include, but are not limited to, antimicrobial agents, chemotherapeutic agents, hormonal agents and anti-hormonal agents. The term "antimicrobial agent" as used in the present invention means antibiotics, antiseptics, disinfectants and other synthetic moieties, and combinations thereof Exemplary chemotherapeutic agents include but are not limited to cis-platinum, paclitaxol, 5-flourouracial, gemcytobine and navelbine. The chemotherapeutic agents are generally grouped as DNA-interactive agents, antimetabolites, tubulin-interactive agents, hormonal agents, hormone-related agents, and others such as asparaginase or hydroxyurea. Hormonal agents include: estrogens, conjugated estrogens and ethinyl estradiol and diethylstilbestrol, chlorotrianisene and idenestrol; progestins such as hydroxyprogesterone caproate, medroxyprogesterone, and megestrol; androgens such as testosterone, testosterone propionate; fluoxymesterone, methyltestosterone; adrenal corticosteroids are derived from natural adrenal cortisol or hydrocortisone. They are used because of their anti-inflammatory benefits as well as the ability of some to inhibit mitotic divisions and to halt DNA synthesis. These compounds include prednisone, dexamethasone, methylprednisolone, and prednisolone. Antihormonal agents include anti-estrogenic agents such as tamosifen, antiandrogen agents such as Flutamide; and antiadrenal agents such as mitotane and amminoglutethimide.

Gene transfer vectors are capable of introducing a polynucleotide into a cell. The polynucleotide may contain the coding sequence of a protein or a peptide, or a nucleotide sequence that encodes an iRNA or antisense RNA. Examples of gene transfer vectors include, but are not limited to, non-viral vectors and viral vectors.

One aspect of the present application relates to an orthopedic fastener for internal fixation of a fractured long bone comprising an IM nail coated on its external surface with a bioabsorbable or biodegradable hydrogel.

In a particular embodiment, the IM nail comprises a center lumen to accommodate a guide wire.

In another particular embodiment, the orthopedic fastener degrades in situ by hydrolytic reactions, enzymatic reactions, alkaline or pH changes.

In another particular embodiment, the IM nail is manufactured from a biodegradable metal or biodegradable alloy. In a related embodiment, the biodegradable metal is magnesium. In another related embodiment, the biodegradable alloy comprises magnesium. In another related embodiment, the biodegradable alloy comprises rare earth materials. In another related embodiment, the biodegradable alloy comprises a magnesium and chitin alloy. In a further related embodiment, the IM nail is made of a chitin and chitosan, N-acylchitosan hydrogel and magnesium alloy with rare earth elements.

In another particular embodiment, the hydrogel is a chitin chitosan, N-acylchitosan hydrogel.

In another particular embodiment, the hydrogel swells to about 30% of its maximal diameter within 10 minutes after coming in contact with moisture.

Another aspect of the present application relates to a method for stabilizing a bone fracture comprising, inserting an orthopedic fastener into the medullary canal of a bone having a fracture, wherein said orthopedic fastener comprises an IM nail coated on its external surface with a bioabsorbable or biodegradable hydrogel.

In a particular embodiment of the method, the orthopedic fastener is placed through the bone cortex.

In another particular embodiment of the method, the orthopedic fastener degrades in situ by hydrolytic reactions, enzymatic reactions, alkaline or pH changes.

Another aspect of the present application relates to a kit for fastener implantation, said kit comprising: an orthopedic fastener for internal fixation of a fractured long bone, comprising an IM nail coated on its external surface with a bioabsorbable or biodegradable hydrogel; a guide wire; and a pusher that is movable along the guide wire.

In a particular embodiment of the kit, the IM nail is made of a bioabsorbable material.

Still another aspect of the present application relates to a kit for fastener implantation in a fractured long bone. The kit includes: an orthopedic fastener comprising an IM nail coated on its external surface with a bioabsorbable or biodegradable hydrogel; a guide wire; and a pusher tube that is movable along the guide wire.

In another particular embodiment of the kit, the IM nail is made with a magnesium core coated with a chitin chitosan, N-acylchitosan hydrogel outer layer.

In another particular embodiment of the kit, the IM nail is made of a chitin and chitosan, N-acylchitosan hydrogel and magnesium alloy with raw earth elements.

K-Wire

Figure 8:
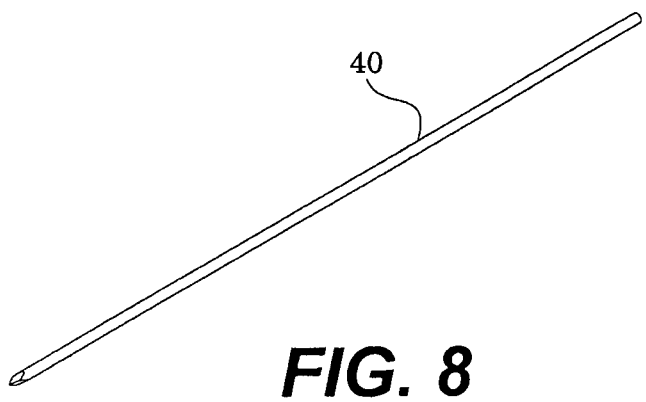
FIG. 8 is an isometric view of an exemplary K-wire.

Another aspect of the present application relates to a Kirschner wire (K-Wire) coated with a hydrogel (coated K-Wire) as described herein for an IM Nail coated with hydrogel. K-wires are sterilized, sharpened, smooth metal or alloy pins that are used to hold bone fragments together (pin fixation) or to provide an anchor for skeletal traction. The pins are often driven into the bone through the skin (percutaneous pin fixation) using a power or hand drill. Following placement of the coated K-Wire, the hydrogel swells, fixing the K-Wire in place in the bone fragments. The swelling of the hydrogel improves the alignment of the fragments and reduces or prevents the migration of the K-Wire. An exemplary K-Wire 40 is shown in FIG. 8.

In particular embodiments, the coated K-Wire comprises a smooth K-Wire. In other embodiments, the coated K-Wire comprises a threaded K-Wire. In still other embodiments, the coated K-Wire comprises a Denham pin.

In some embodiments, the K-Wire is made of a durable metal. In particular further embodiments, the durable metal is stainless steel. In another embodiment, the durable metal is titanium. In a further embodiment, the durable metal is an alloy comprising titanium. In a still further embodiment, the alloy comprises titanium and nickel. In a yet still further embodiment, the alloy comprising titanium and nickel is nitinol.

In some embodiments, the K-Wire is manufactured from a biodegradable metal or biodegradable alloy. In a further embodiment, the biodegradable metal is magnesium. In another further embodiment, the biodegradable alloy comprises magnesium. In a still further embodiment, the magnesium alloy additionally includes rare earth materials. In another or related still further embodiment, the biodegradable alloy comprises a magnesium alloy and chitin. In another or related still further embodiment, the biodegradable alloy comprises a magnesium and chitin alloy. In a yet further embodiment, the K-Wire is made of a chitin and chitosan, N-acylchitosan hydrogel and magnesium alloy with rare earth elements.

In some embodiments, the hydrogel coating of the K-Wire is a chitin chitosan, N-acylchitosan hydrogel. In particular embodiments, the hydrogel may absorb moisture and expand in situ at the treatment site. For example, the hydrogel would swell once it comes into contact with various body fluids. As used herein, the "pre-implantation diameter Dpre" refers to the largest diameter of a coated K-Wire before implantation and the "post-implantation diameter Dpost" refers to the largest diameter of the coated K-Wire after implantation.

In some embodiments, the hydrogel coating of the K-Wire swells to about 10-90% of its maximal diameter within 10, 20 or 30 minutes after coming in contact with moisture. In some embodiments, the hydrogel swells to about 10% of its maximal diameter within 10, 20 or 30 minutes after coming in contact with moisture. In some embodiments, the hydrogel swells to about 20% of its maximal diameter within 10, 20 or 30 minutes after coming in contact with moisture. In some embodiments, the hydrogel swells to about 30% of its maximal diameter within 10, 20 or 30 minutes after coming in contact with moisture. In some embodiments, the hydrogel swells to about 40% of its maximal diameter within 10, 20 or 30 minutes after coming in contact with moisture. In some embodiments, the hydrogel swells to about 50% of its maximal diameter within 10, 20 or 30 minutes after coming in contact with moisture. The hydrogel swells or expands by absorbing of fluids and improves the union and support of the bone fragments.

In particular embodiments, the coated K-Wire is attached to an external fixation device.

In particular embodiments, the coated K-Wire is trimmed following emplacement, such that the end of the coated K-Wire does not protrude from the bone or bone fragment.

Bone Screw

Figure 9:
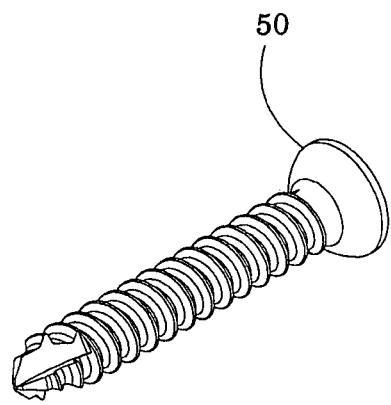
FIG. 9 is an isometric view of an exemplary bone screw.

Another aspect of the present application relates to a bone screw coated with a hydrogel as described herein for an IM Nail coated with hydrogel. Bone screws, such as Scaphoid screws, are screws used to fix bone fractures. The bone screw has threads on both ends of the screw and is placed completely inside the bone to hold the fractured pieces together. Following placement of the coated bone screw, the hydrogel swells, fixing the bone screw in place in the bone fragments. The swelling of the hydrogel improves the alignment of the fragments and reduces or prevents the migration of the bone screw. In one embodiment, the bone screw is a Scaphoid screw for fixation of a fractured carpal bone or tarsal bone. Scaphoid fractures are the most common fracture of a carpal bone, representing about 2-7% of all fractures and over 70% of all hand fractures presenting to emergency departments. An exemplary bone screw 50 is shown in FIG. 9.

In some embodiments, the bone screw is made of a durable metal. In particular further embodiments, the durable metal is stainless steel. In another embodiment, the durable metal is titanium. In a further embodiment, the durable metal is an alloy comprising titanium. In a still further embodiment, the alloy comprises titanium and nickel. In a yet still further embodiment, the alloy comprising titanium and nickel is nitinol.

In another particular embodiment, the bone screw is manufactured from a biodegradable metal or biodegradable alloy. In a related embodiment, the biodegradable metal is magnesium. In another related embodiment, the biodegradable alloy comprises magnesium. In another related embodiment, the biodegradable alloy comprises rare earth materials. In another related embodiment, the biodegradable alloy comprises a magnesium alloy and chitin. In another related embodiment, the biodegradable alloy comprises a magnesium and chitin alloy. In a further related embodiment, the bone screw is made of a chitin and chitosan, N-acylchitosan hydrogel and magnesium alloy with rare earth elements.

In some embodiments, the hydrogel coating of the bone screw is a chitin chitosan, N-acylchitosan hydrogel. In particular embodiments, the hydrogel may absorb moisture and expand in situ at the treatment site. For example, the hydrogel would swell once it comes into contact with various body fluids. As used herein, the "pre-implantation diameter Dpre" refers to the largest diameter of a coated bone screw before implantation and the "post-implantation diameter Dpost" refers to the largest diameter of the largest diameter of the coated bone screw is capable to reach after implantation.

In some embodiments, the hydrogel coating of the bone screw swells to about 10-90% of its maximal diameter within 10, 20 or 30 minutes after coming in contact with moisture. In some embodiments, the hydrogel swells to about 10% of its maximal diameter within 10, 20 or 30 minutes after coming in contact with moisture. In some embodiments, the hydrogel swells to about 20% of its maximal diameter within 10, 20 or 30 minutes after coming in contact with moisture. In some embodiments, the hydrogel swells to about 30% of its maximal diameter within 10, 20 or 30 minutes after coming in contact with moisture. In some embodiments, the hydrogel swells to about 40% of its maximal diameter within 10, 20 or 30 minutes after coming in contact with moisture. In some embodiments, the hydrogel swells to about 50% of its maximal diameter within 10, 20 or 30 minutes after coming in contact with moisture. The hydrogel swells or expands by absorbing of fluids and improves the connection and support of the inner wall of the bone canal.

The present invention is further illustrated by the following example which should not be construed as limiting. The contents of all references, patents and published patent applications cited throughout this application, as well as the Figures and Tables, are incorporated herein by reference.

EXAMPLE 1

Fixation of a Tibial Fracture

The subject is positioned on an operating or extension table in the supine position. The knee of the injured leg is flexed at least through ninety degrees and a femoral holding device may be applied.

The entry point of the orthopedic fastener lies in the prolongation of the axis of the diaphysis at the upper margin of the tibia. A longitudinal incision of about 25 mm is made at the lower margin of the patella.

The tip of a guide rod is placed at the entry point and driven forward through the bone into the medullary canal. A tissue protection sleeve is placed over the guide rod and moved into contact with the external surface of the bone.

Inside the tissue protection sleeve, a cannulated awl is driven forward over the guide wire with rotating movements in order to make the hole large enough for the insertion of the orthopedic fastener.

The awl, tissue protection sleeve and guide rod are removed. A guide wire is inserted into the medullary canal, pushed forward into the distal fragment and positioned centrally in the distal tibial metaphysis.

The orthopedic fastener is inserted by hand over the guide wire into the medullary canal and a pusher, such as a slap hammer, is inserted onto the guide wire. The orthopedic fastener is driven completely into the medullary canal using the pusher.

The guide wire is removed and the hydrogel is allowed sufficient time to expand in the medullary canal and align the ends of the fragments.

The position of the orthopedic fastener in the tibia is fixed by applying set screws through the bone into the distal and proximal regions of the IM nail.

Subsequently, following sufficient time for knitting of the bone at the fracture site, the set screws are removed and the orthopedic fastener is allowed to remain in the medullary canal for support of the bone until the orthopedic fastener is bioabsorbed by the subject's body.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An orthopedic fastener for internal fixation of a fractured long bone, comprising:
 a biodegradable or bioabsorbable intramedullary (IM) nail comprising an elongated body with an external surface and a hollow center lumen passageway,
 wherein the external surface is sufficiently coated with a bioabsorbable or biodegradable hydrogel so that upon implantation in a medullary canal, the hydrogel swells and fills the canal, creating an internal soft fixation of the fracture, thereby assisting with the realignment of the displaced bone fracture, and
 wherein the IM nail is made from a biodegradable magnesium alloy and the hydrogel comprises chitin, chitosan, N-acylchitosan, or a combination thereof.

2. The orthopedic fastener of claim 1, wherein agents or cells are embedded into the hydrogel coating.

3. The orthopedic fastener of claim 1, wherein the biodegradable magnesium alloy comprises rare earth materials.

4. The orthopedic fastener of claim 1, wherein the hydrogel swells to about 30% of its maximal diameter within 10 minutes after coming in contact with moisture.

5. The orthopedic fastener of claim 1, wherein the fastener has multiple reservoirs, one inside the other, wherein when an outer layer of a reservoir is absorbed, another reservoir comprising agents or cells disposed therein is exposed, thereby allowing for the release of the agents or cells disposed therein.

6. The orthopedic fastener of claim 1, wherein the hydrogel comprises at least two of chitin, chitosan, and N-acylchitosan.

7. The orthopedic fastener of claim 6, wherein the hydrogel comprises chitin, chitosan and N-acylchitosan.

8. The orthopedic faster of claim 1, wherein the IM nail has a proximal end and a distal end, and wherein the passageway extends longitudinally from the proximal end to the distal end and is the only passageway extending through the IM nail.

9. An orthopedic fastener device for fixation of a fractured bone comprising a biodegradable or bioabsorbable K-Wire sufficiently coated on its external surface with a bioabsorbable or biodegradable hydrogel so that upon implantation in a medullary canal, the hydrogel swells and fills the canal, creating an internal soft fixation of the fracture, thereby assisting with the realignment of the displaced bone fracture, wherein the K-Wire is made from a biodegradable magnesium alloy and the hydrogel comprises chitin, chitosan, N-acylchitosan, or a combination thereof.

10. An orthopedic fastener device for fixation of a fractured bone, comprising a biodegradable or bioabsorbable bone screw sufficiently coated on its external surface with a bioabsorbable or biodegradable hydrogel so that upon implantation in a medullary canal, the hydrogel swells and fills the canal, creating an internal soft fixation of the fracture, thereby assisting with the realignment of the displaced bone fracture, wherein the bone screw is made from a biodegradable magnesium alloy and the hydrogel comprises chitin, chitosan, N-acylchitosan, or a combination thereof.

11. The orthopedic fastener device of claim 10, wherein said bone screw is a Scaphoid screw for fixation of a fractured carpal or tarsal bone.

* * * * *